(12) United States Patent
Blake et al.

(10) Patent No.: US 7,458,957 B2
(45) Date of Patent: Dec. 2, 2008

(54) UNIVERSAL VALVE FOR FOLEY TYPE URINARY CATHETER

(75) Inventors: William S. Blake, Linwood, NJ (US); William J. Dwyer, 18 Angela Cir., Hazlet, NJ (US) 07730

(73) Assignee: William J. Dwyer, Hazlet, NJ (US)

( * ) Notice: Subject to any disclaimer, the term of this patent is extended or adjusted under 35 U.S.C. 154(b) by 401 days.

(21) Appl. No.: 11/083,240

(22) Filed: Mar. 17, 2005

(65) Prior Publication Data

US 2006/0212024 A1 Sep. 21, 2006

(51) Int. Cl.
*A61M 1/00* (2006.01)
*A61M 25/16* (2006.01)
*A61F 5/44* (2006.01)

(52) U.S. Cl. ............... 604/323; 604/335; 604/350; 604/537

(58) Field of Classification Search ............ 604/317, 604/323, 335, 350, 264, 523, 533, 537
See application file for complete search history.

(56) References Cited

U.S. PATENT DOCUMENTS

| | | | | |
|---|---|---|---|---|
| 2,494,477 A | * | 1/1950 | Kurtz | 604/347 |
| 3,331,371 A | * | 7/1967 | Rocchi et al. | 604/99.04 |
| 4,432,757 A | * | 2/1984 | Davis, Jr. | 604/99.02 |
| 4,932,938 A | * | 6/1990 | Goldberg et al. | 604/99.04 |
| 4,946,449 A | * | 8/1990 | Davis, Jr. | 604/256 |
| 5,087,252 A | * | 2/1992 | Denard | 604/346 |
| 5,169,393 A | * | 12/1992 | Moorehead et al. | 604/247 |
| 5,445,626 A | * | 8/1995 | Gigante | 604/349 |
| 6,050,934 A | * | 4/2000 | Mikhail et al. | 600/30 |
| 6,767,340 B2 | * | 7/2004 | Willis et al. | 604/256 |
| 7,037,303 B2 | * | 5/2006 | Beaufore et al. | 604/537 |
| D546,946 S | * | 7/2007 | Blake et al. | D24/129 |

* cited by examiner

*Primary Examiner*—Tatyana Zalukaeva
*Assistant Examiner*—Michael G Bogart
(74) *Attorney, Agent, or Firm*—Robert M. Skolnik

(57) ABSTRACT

A universal valve for the Foley type urinary catheter has structure which permits its use as a patient controlled drainage valve, as an interface from which to take sterile samples, and as a connection to a day or night collection bag all without removal of the universal valve from the Foley type urinary catheter. The universal valve may be open or closed by the use of a squeeze mechanism for patient control, or by movement of the threaded connection between the universal valve and a collection bag so that the universal valve is continuously open for drainage into the urine collection bag.

6 Claims, 7 Drawing Sheets

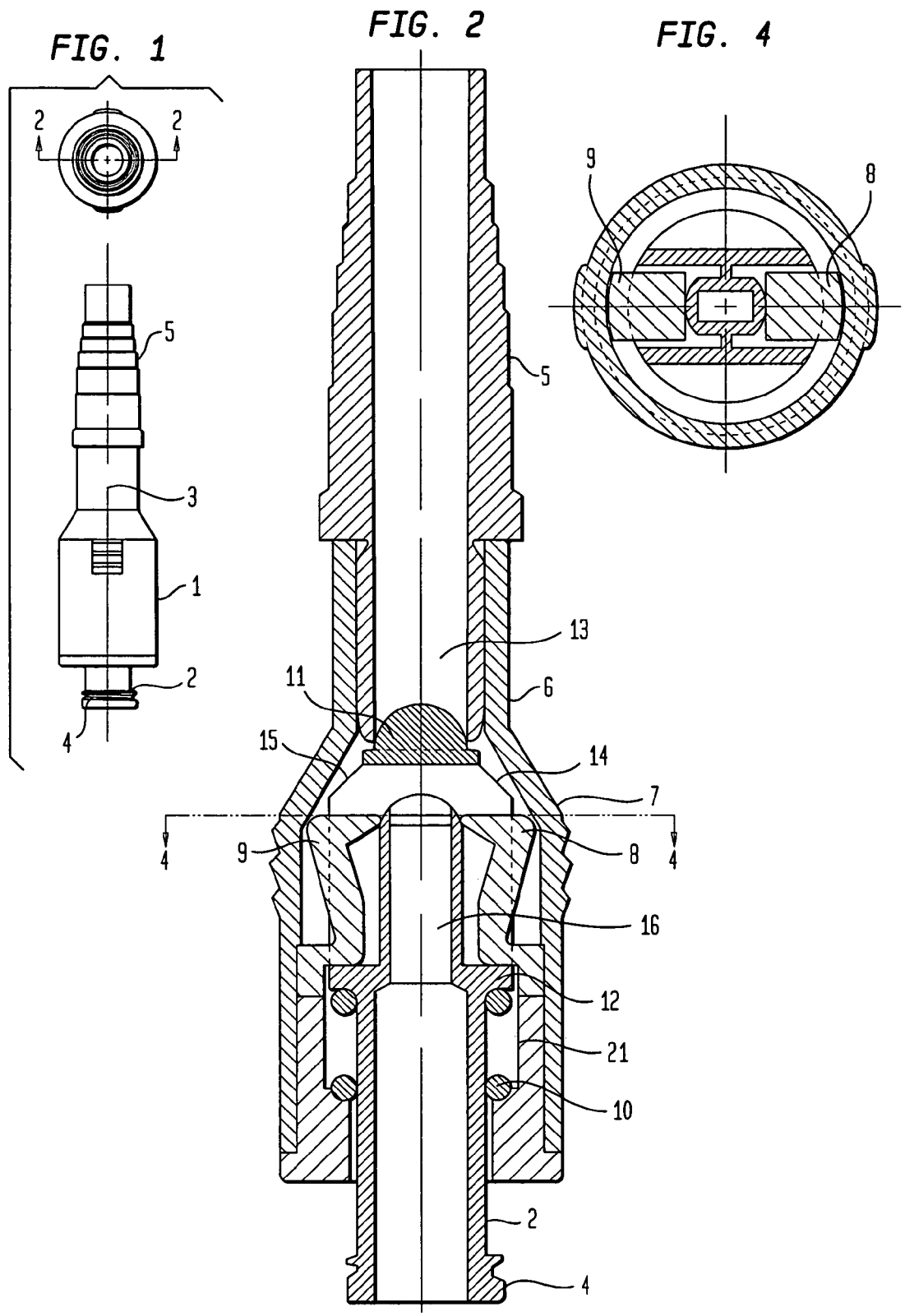

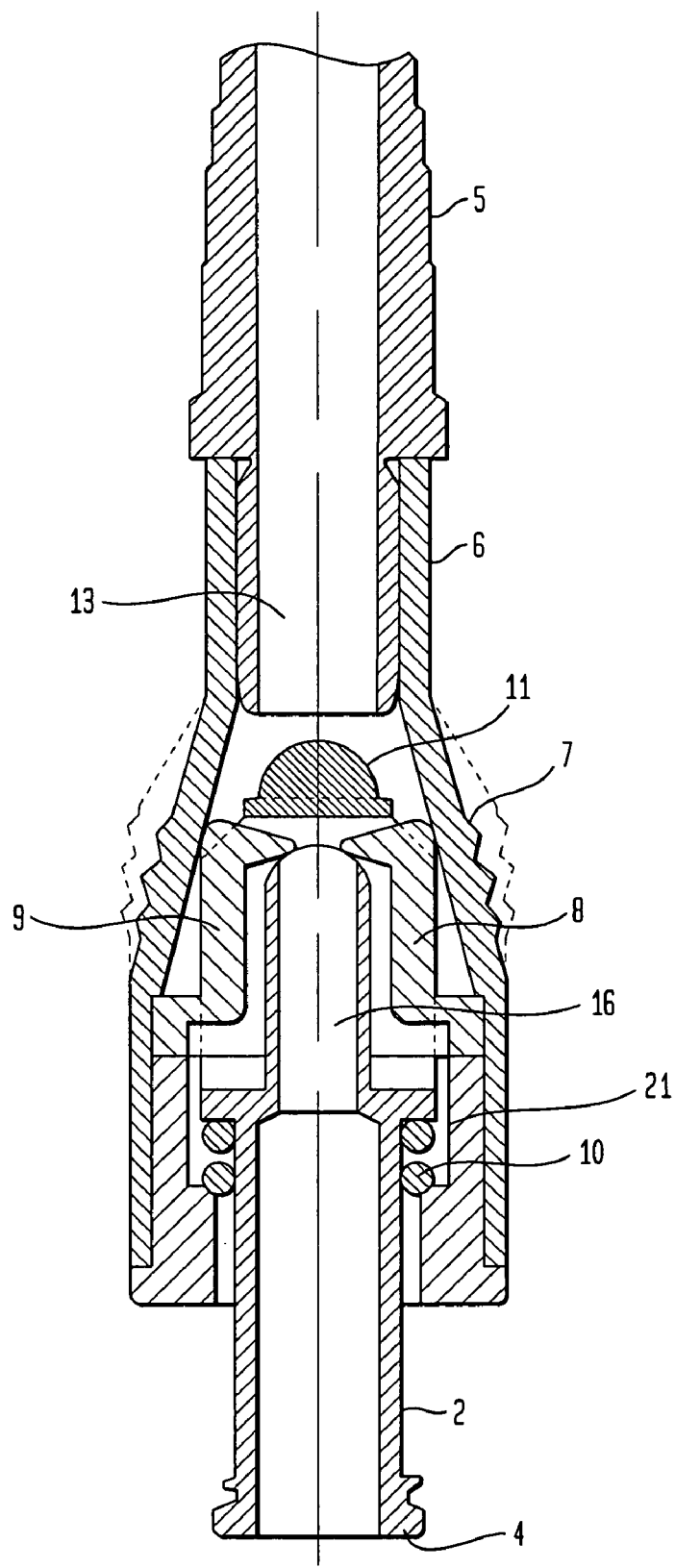

UNIVERSAL VALVE FOR FOLEY TYPE URINARY CATHETER

BACKGROUND OF THE INVENTION

1. Field of the Invention

The present invention relates a universal valve for a Foley type urinary catheter, which permits clinical extraction of sterile samples, patient controlled drainage, urinary retention, patient freedom and mobility, and automatic drainage by connection to a urine collection bag.

2. Description of the Related Art

U.S. Pat. No. 2,494,477, Kurtz shows a manually operable valve to drain collected urine when convenient in a shorts type garment.

U.S. Pat. No. 3,331,371, Rocchi, et al. show a structure for providing the dignity to the catheter patient with a drainage valve.

U.S. Pat. No. 4,432,757 Davis discloses a Foley catheter having a valve for control by the patient.

U.S. Pat. No. 4,932,938 Goldberg, et al. disclose a combined user controlled and continuous drainage catheter.

U.S. Pat. No. 4,946,449 Davis is another free drainage and valve controlled catheter.

U.S. Pat. No. 5,087,252 Denard also shows an on-off valve to provide user dignity.

U.S. Pat. No. 5,445,626 Gigante shows a specific valve structure, which is stated to provide ease of use to a patient.

U.S. Pat. No. 6,050,934 Mikhail, et al. at columns 1-4 provide a tutorial on the technical history of the proposed modifications to the Foley type catheter and the advantages and disadvantages of each.

SUMMARY OF THE INVENTION

The present invention is a universal valve for the Foley type urinary catheter. The universal valve has structure which permits its use as a patient controlled drainage valve, as an interface from which to take sterile samples, and as a connection to a day or night collection bag all without removal of the valve from the Foley type urinary catheter.

The valve may be open or closed by the use of a squeeze mechanism for patient control, or by movement of a connection between the valve and a collection bag so that the valve is continuously open for drainage into the urine collection bag.

Use of the universal valve of this invention increases patient mobility as well as patient dignity because of the patient's ability to control flow. This control also makes the valve suited for use in establishing bladder control for patients whose mental and/or physical states are such that they are capable of such control.

Use of the universal valve also allows for patient self-control of urinary bladder retention.

The foregoing, as well as further objects and advantages of the invention will become apparent to those skilled in the art from a review of the following detailed description of my invention, reference being made to the accompanying drawings.

BRIEF DESCRIPTION OF THE DRAWINGS

FIG. 1 is a side view of the preferred embodiment of the invention:

FIG. 2 is a sectional view taken along the line 2-2 of FIG. 1 with the valve closed;

FIG. 3 is a sectional view of the similar to that shown in FIG. 1 with the valve open;

FIG. 4 is a sectional view taken along the line 4-4 of FIG. 2;

DETAILED DESCRIPTION OF THE PREFERRED EMBODIMENT

Figure 5:
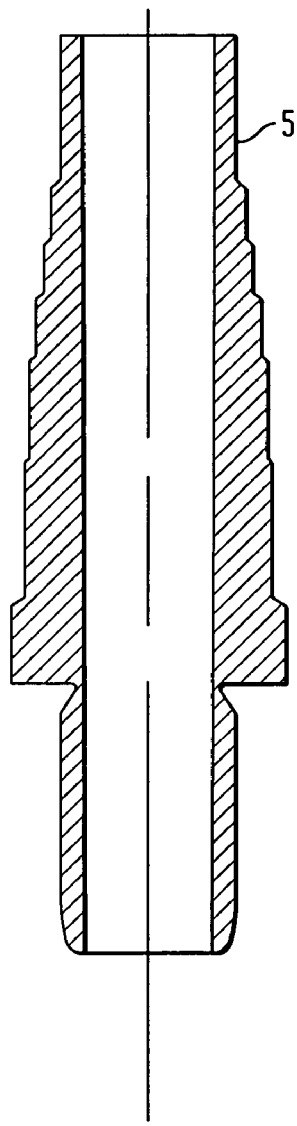
FIG. 5 is a sectional view of the stepped connector of FIG. 2.

Like reference numerals have been used to designate like parts in all figures. As shown in FIG. 1, the valve assembly includes a barrel housing 1 which may have an aperture formed therein in area 3 in which is mounted an injectable mesh material. The barrel housing 1 is connected to LEUR® lock assembly 2, 4 for connecting the universal valve to a urine collection bag. The narrower diameter stepped section 5 is the adapter interface used to connect the universal valve to the Foley catheter. Stepped section 5 is formed integrally with the flex body 7 and is the fluid input to the universal valve while section 2 is the fluid output from the universal valve.

FIG. 2 is a sectional view taken along the line 2-2 of FIG. 1. It shows the spring-loaded floating pintle seal valve 11 in its closed position. FIG. 3 shows the same seal valve 11 in its open position. As will be explained in detail below, the seal may be open or closed by squeezing the outer housing or by pulling and holding the LEUR® lock fitting, 2, 4.

In FIG. 2, numeral 5 shows the connector for connecting the Foley catheter (not shown) to the pintle seal assembly. Connector 5 is a stepped connector known as a catheter adapter and is used to connect the universal valve to the Foley catheter tubing. A sectional view of this connector is shown in FIG. 5. A pintle 11 is held into the central opening 13 of the catheter adapter connector 5 to close the opening 13. Pintle 11 is formed on walls 14, 15 surrounding moveable round member 16. Member 16 is moveable by manually squeezing actuating tongs 8 and 9 through flex body 7. Squeezing the tongs causes them to push the domed round member 16 downward against the force of compression spring 10, which in turn moves the pintle 11 from the closed position shown in FIG. 2 to the open position shown in FIG. 3. When the tongs are released, the spring 10 causes the pintle to return to its closed position.

FIG. 3 is a view similar to FIG. 1 showing the pintle valve 11 open. Tongs 8, 9 are shown covering the domed portion of round member 16. Spring 10 is shown compressed against the assembly retainer plug 21, shown in detail in FIGS. 10-10B, and the ledge portion 12 of the pintle valve. The closed position is maintained either manually, by hand pressure on serrated pads formed on flex body 7, 180° apart, or continuously held by the connection of LEUR® lock to its adapter for connection to urine collection bag.

Figure 6:
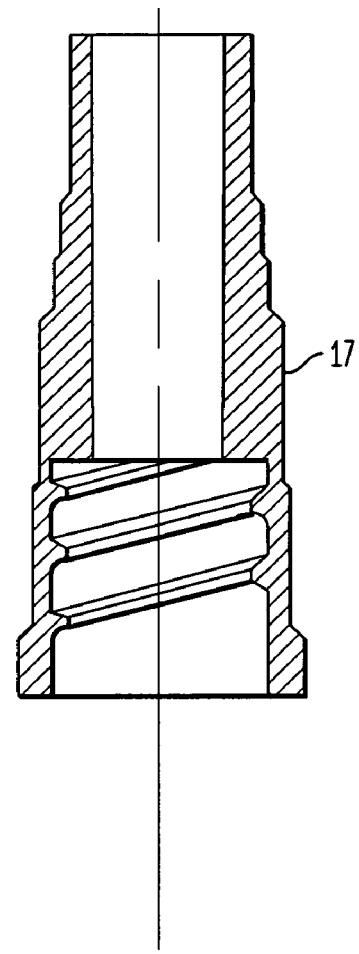
FIG. 6 is a sectional view of the LEUR® lock adapter.
Figure 7:
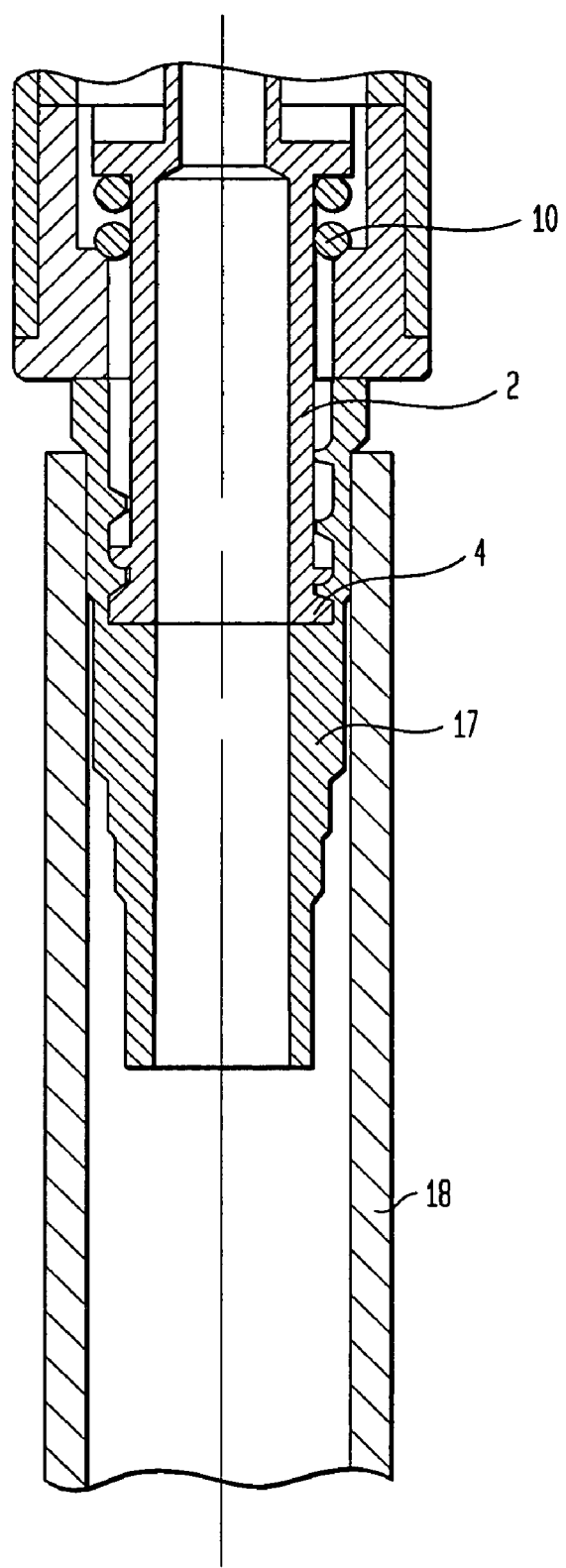
FIG. 7 is a sectional view of the adapter of FIG. 6 connected to the preferred embodiment of FIG. 1 and to collection bag tubing.

FIG. 4 is a sectional view taken along the line 4-4 of FIG. 3 showing the top surfaces of tongs 8 and 9, FIG. 6, is a sectional view of the LEUR® lock adapter 17 which fits onto connection 2, 4 of FIGS. 2, 3. When threadedly engaged, adapter 17 serves to hold the pintle 11 in the open position shown in FIG. 3. This is illustrated in detail in FIG. 7 where adapter 17 is threaded onto threads 3 and tightened to the position shown in FIG. 7. Numeral 18 denotes a section of tubing to connect the universal valve to urine collection bag.

Figure 8B:
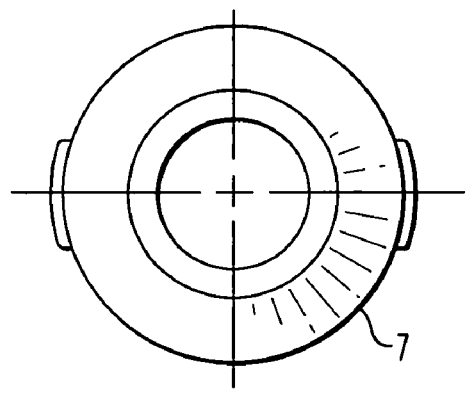
FIGS. 8-8B are sectional, bottom and top views, respectively, of the actuator flex body of FIGS. 2-3.
Figure 8:
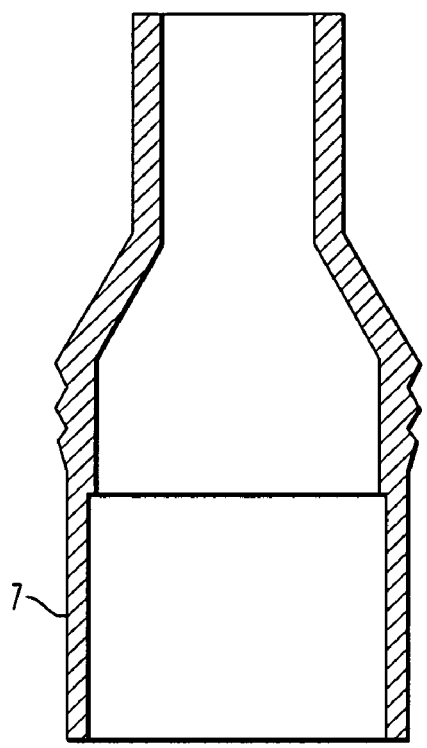
Figure 8A:
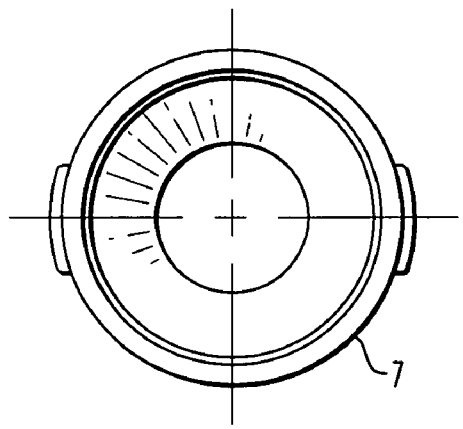

FIGS. 8-8B show a sectional view of flex body 7, a bottom view of same (FIG. 8A) and a top view of same (FIG. 8B).

Figure 9B:
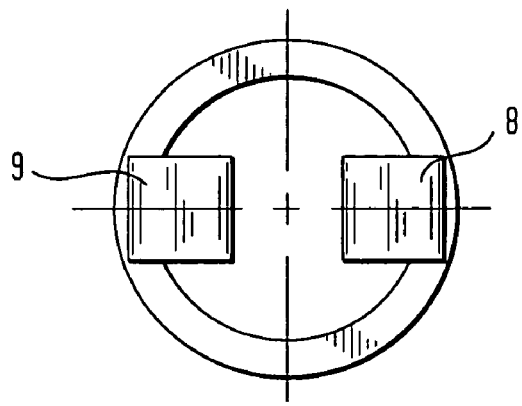
FIGS. 9-9C are detailed views of the actuator tongs of FIGS. 2-3.
Figure 9:
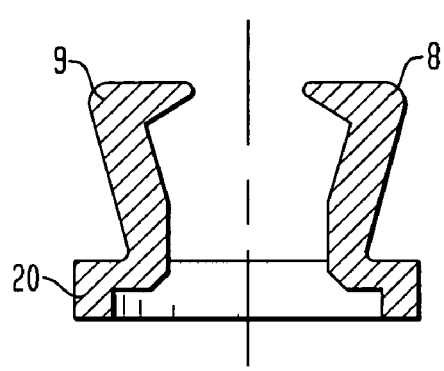
Figure 9C:
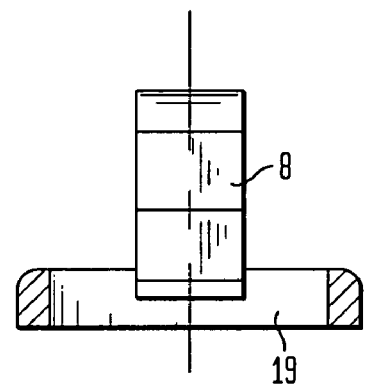
Figure 9A:
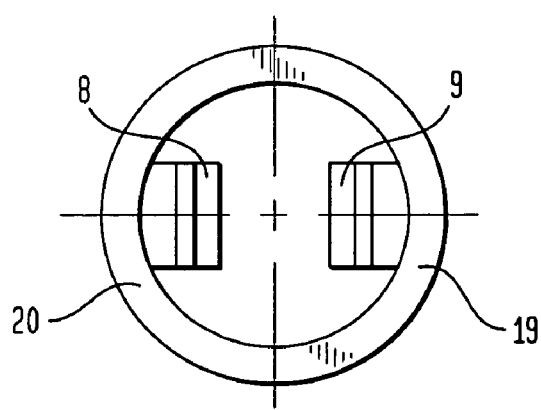

FIGS. 9A-9C show views of the actuator tongs 8, 9. Each tong is formed within a round base 19, for tong 8 and 20 for tong 9.

Figure 10A:
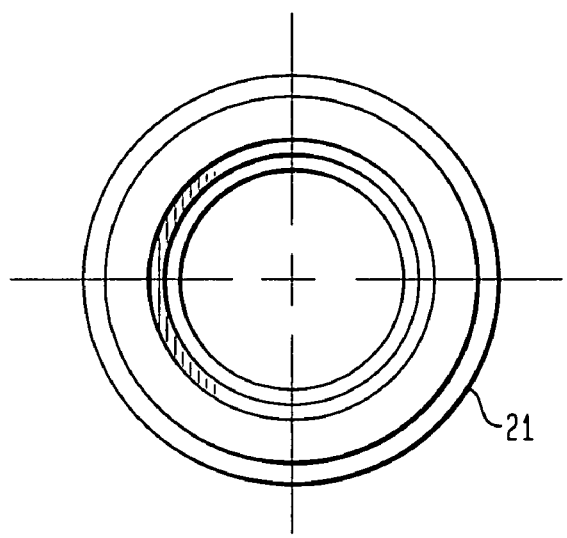
FIGS. 10-10B are detailed views of the retainer plug of FIGS. 2-3.
Figure 10:
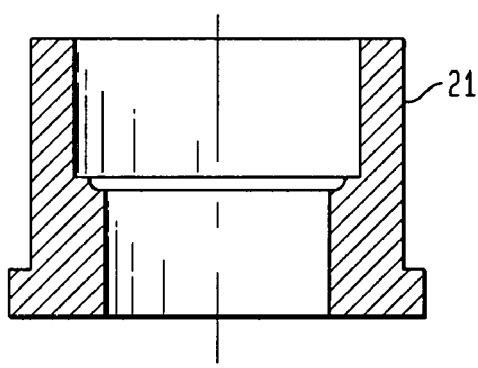
Figure 10B:
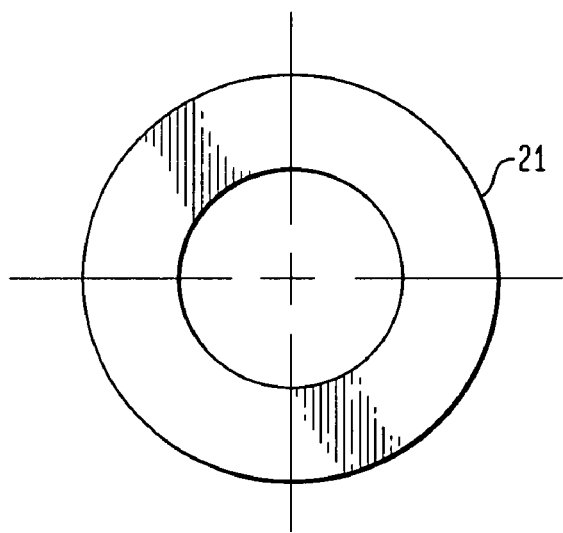

FIGS. 10-10B are detailed views of the retainer plug 21 of FIGS. 2-3.

Further modifications to the invention may be made without departing from the spirit and scope of the invention; accordingly, what is sought to be protected is set forth in the appended claims.

What is claimed is:

1. A universal valve for a Foley type urinary catheter comprising: a body having a central through aperture formed therein, a hollow connector formed at one end of said body for connecting said aperture to a Foley type urinary catheter; valve means mounted in said body for opening and closing said central aperture; said body having manually squeezable means formed adjacent to said valve means for opening and closing said valve means; connection means formed at the other end of said body for connecting said aperture to a collection bag; coupling means for coupling said connection means to said valve to maintain said valve means in an open position when said universal valve is connected to a collection bag and closing said valve means when said universal valve is not connected to a collection bag and an opening formed in said body, said opening being covered by mesh material for permitting the passage of a needle there through to obtain a sample of fluid from said central aperture.

2. A universal valve for a Foley type urinary catheter comprising: a body having a central through aperture formed therein, a hollow connector formed at one end of said body for connecting said aperture to a Foley type urinary catheter; valve means mounted in said body for opening and closing said central aperture; said body having manually squeezable means formed adjacent to said valve means for opening and closing said valve means; connection means formed at the other end of said body for connecting said aperture to a collection bag; coupling means for coupling said connection means to said valve to maintain said valve means in an open position when said universal valve is connected to a collection bag and closing said valve means when said universal valve is not connected to a collection bag said valve means including a pintle formed on a flexible support, a compression spring surrounding said central aperture, a retainer plug attached to said flexible support; said compression spring being held between said retainer plug and a portion of said flexible support, and contacting means for contacting said flexible support for moving said pintle to open and close said central aperture.

3. The universal valve of claim 2 wherein said contacting means includes a pair of tongs mounted beneath said manually squeezable means, said tongs being squeezed into engagement with said flexible support to open said valve means.

4. The universal valve of claim 2 wherein said coupling means is attached to said flexible support for moving said support against the force of said spring when said universal valve is connected to a collection bag.

5. The universal valve of claim 4 further including adapter means threadedly engaging said coupling means for connecting said valve to a collection bag.

6. The universal valve of claim 3 wherein said flexible support includes a domed portion for engaging said tongs.

* * * * *